United States Patent
Chang et al.

(10) Patent No.: US 10,481,141 B2
(45) Date of Patent: Nov. 19, 2019

(54) LEVERAGING AIR/WATER CURRENT VARIABILITY FOR SENSOR NETWORK VERIFICATION AND SOURCE LOCALIZATION

(71) Applicant: INTERNATIONAL BUSINESS MACHINES CORPORATION, Armonk, NY (US)

(72) Inventors: Josephine B. Chang, Bedford Hills, NY (US); Hendrik F. Hamann, Yorktown Heights, NY (US); Siyuan Lu, Yorktown Heights, NY (US); Ramachandran Muralidhar, Mahopac, NY (US); Theodore G. Van Kessel, Millbrook, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 271 days.

(21) Appl. No.: 15/632,857

(22) Filed: Jun. 26, 2017

(65) Prior Publication Data

US 2017/0292938 A1    Oct. 12, 2017

Related U.S. Application Data

(63) Continuation of application No. 15/017,943, filed on Feb. 8, 2016, now Pat. No. 9,766,220.

(51) Int. Cl.
*G01N 33/00* (2006.01)
*G01N 33/18* (2006.01)
*G01P 5/00* (2006.01)

(52) U.S. Cl.
CPC ....... *G01N 33/0062* (2013.01); *G01N 33/007* (2013.01); *G01N 33/0031* (2013.01);
(Continued)

(58) Field of Classification Search
CPC .......... G01N 33/0062; G01N 33/0031; G01N 33/0036; G01N 33/007; G01N 33/0075; G01N 33/18; G01P 5/00
See application file for complete search history.

(56) References Cited

U.S. PATENT DOCUMENTS

| 6,895,335 B2 | 5/2005 | Archibald et al. |
| H2208 H | 1/2008 | Stytz et al. |

(Continued)

OTHER PUBLICATIONS

Bychkovskiy et al., "A Collaborative Approach to In-Place Sensor Calibration", F. Zhao and L. Guibas (Eds.): IPSN 2003, LNCS 2634, pp. 301-316, 2003 (Year: 2003).*

(Continued)

*Primary Examiner* — Regis J Betsch
(74) *Attorney, Agent, or Firm* — Tutunjian & Bitetto, P.C.; Vazken Alexanian

(57) ABSTRACT

A method for measuring pollution that includes providing a plurality of analyte sensors arranged in a grid over a sensing area, wherein the analyte sensors measure a pollutant, and positioning at least one current sensor in the sensing area. A pollution source is localized using a pollution source locator including a dispersion model and at least one hardware processor to interpolate a location of a pollution source from variations in current measured from the current sensors and measurements of pollutants from the analyte sensors.

20 Claims, 6 Drawing Sheets

(52) U.S. Cl.
CPC ..... *G01N 33/0036* (2013.01); *G01N 33/0075* (2013.01); *G01N 33/18* (2013.01); *G01P 5/00* (2013.01)

(56) References Cited

U.S. PATENT DOCUMENTS

| | | |
|---|---|---|
| 7,375,642 B2 | 5/2008 | Siemens et al. |
| 7,523,638 B2 | 4/2009 | Prince |
| 7,834,754 B2 * | 11/2010 | Kulesz ................ G08B 21/12 340/506 |
| 8,838,271 B2 | 9/2014 | Ghose et al. |
| 8,949,037 B2 | 2/2015 | Prince et al. |
| 2014/0238107 A1 | 8/2014 | Chou et al. |

OTHER PUBLICATIONS

Huang et al., "Sources Detection and Parameters Estimation of Plume Model Based on Sensor Network Measurements", Technical Report 08-07, Department of Statistics, Indiana University Nov. 9, 2008 (Year: 2008).*

List of IBM Patents or Patent Applications Treated as Related dated Jun. 26, 2017, 2 pages.

Zhuk, S. et al., "On gas leak source localisation under incomplete knowledge of wind field" IBM Research (Apr. 27, 2015) pp. 1-18.

Sahyoun, S. "Plume Source Localization and Boundary Prediction" Master's Thesis, University of Tennessee (Aug. 2009) http://trace.tennessee.edu/utk_gradthes/61.

Li, W. et al., "Localization of the offshore pollutant source in lakes using spatial-temporal filtering" Proceedings of the 33rd Chinese Control Conference (CCC), (Jul. 28-30, 2014) pp. 371-376.

* cited by examiner

LEVERAGING AIR/WATER CURRENT VARIABILITY FOR SENSOR NETWORK VERIFICATION AND SOURCE LOCALIZATION

BACKGROUND

Technical Field

The present disclosure relates to determining the location of pollution sources, and more particularly to measuring pollution sources taking into account air and/or water current changes.

Description of the Related Art

Pollution technologies, including smart grid, and pollution mitigation, have become a policy focus in developed and developing nations. Air pollution is a mixture of solid particles and gases in the air. Water pollution is the contamination of water bodies (e.g. lakes, rivers, oceans, aquifers and groundwater). This form of environmental degradation occurs when pollutants are directly or indirectly discharged into water bodies without adequate treatment to remove harmful compounds.

SUMMARY

In one embodiment, the present disclosure provides a method of determining the source of pollutants. The method may include providing a plurality of analyte sensors arranged in a grid over a sensing area, wherein the analyte sensors measure a pollutant relative to a background reading. At least one current sensor is positioned in the sensing area, wherein changes in current are measured with the current sensor. A pollution source is localized by a pollution source locator including a dispersion model and at least one hardware processor to interpolate a location of a pollution source from variations in current measured from the current sensors and measurements of pollutants from the analyte sensors from sites on the grid that are above the background reading.

In another aspect of the present disclosure, a system for determining the source of an air pollutant is provided. In one embodiment, the system includes a receiver for receiving measurements of current variations from a current sensor positioned in the sensing area, and for receiving pollutant measurements from a plurality of analyst sensors positioned on a grid of the sensing area. The system further includes a sensor validator that determines using current measurements whether the analyst sensors are functioning and calibrated. The system further includes a pollution source locator including a dispersion model and at least one hardware processor to interpolate a location of a pollution source from variations in current measured from the current sensors and measurements of pollutants from the analyte sensors from sites on the grid that are above a background reading.

In yet another embodiment, a non-transitory computer readable storage medium is provided that includes a computer readable program for determining a source of air pollution. The computer readable program when executed on a computer causes the computer to perform the steps of receiving measurements of current variations from a current sensor positioned in a sensing area, and receiving pollutant measurements from a plurality of analyst sensors positioned on a grid of the sensing area. Determining at high current values received from the current variations whether the analyte sensors are calibrated, wherein calibrated analyte sensors read a uniform background reading at said high current values. The method further includes localizing a pollution source with a pollution source locator including a dispersion model and at least one hardware processor to interpolate a location of a pollution source from variations in current measured from the current sensors and measurements of pollutants from the analyte sensors from sites on the grid that are above the background reading.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
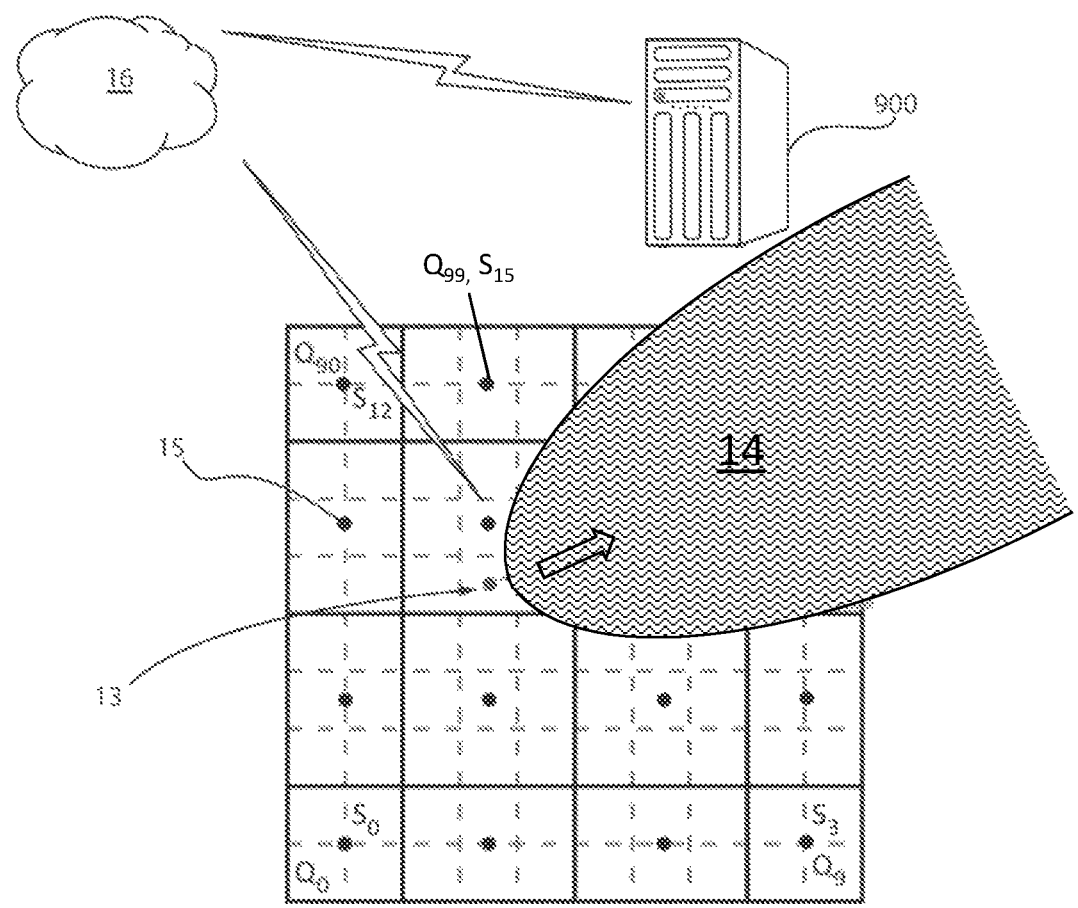
FIG. 1 is a schematic of a grid of sensors across a leak area for determining a source of an air pollutant/water pollutant, in accordance with one embodiment of the present disclosure.

Detailed embodiments of the claimed methods, structures and computer products are disclosed herein; however, it is to be understood that the disclosed embodiments are merely illustrative of the claimed structures and methods that may be embodied in various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure. Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

The present disclosure provides for the detection and localization of sources of air and water pollution, i.e., provides for air/water quality monitoring and leak detection. A number of source localization methods exist that model the "forward problem", e.g., dispersion of a plume of gas from a source, given leak rate, gas and atmospheric density, wind, etc. However, solving the backwards problem in which source location and leak size are to be inferred from fixed location sensors readings presents greater difficulty, especially when the precision of localization desired is much greater than the density of sensors available. Sensor validation is an important problem in sensor network system developments. Maintenance is a significant driver of cost, and should be minimized for low-cost systems. However, drift is a well-known weakness of nearly all physical sensing systems, and operation of commercial sensors specify a finite operation time before the sensor must be recalibrated. It has been determined that false positives are another frequent driver of cost for sensor network applications, and must be minimized. Drift in a sensor's "zero" reading is thus the most important situation to avoid for proper operation of a sensor network.

The methods, systems, and computer program products that are disclosed leverages the inherent speed and direction variability of air and/or water currents in natural settings for sensor network verification and source localization. By natural setting it is meant that the methods and systems disclosed herein can be used in a typical out doors setting which is susceptible to wind changes or water current changes, as opposed to a laboratory setting or a wind chamber setting, in which variations in wind or current are not present. The variability in wind and or current changes refers to the changes in the direction and speed of the wind or water current. These wind and current conditions may be normal weather patterns, or they may be patterns impacted by an external source, such as a man-made interaction, e.g., vehicle movement. As will be discussed below, the systems employed, such as those used in the disclosed method, may include (1) physical sensors (e.g. gas or chemical sensors and co-located air/water current speed and direction sensors) placed in an environment with variable air/water current speeds and directions, (2) a network which collects data from the physical sensors to a central analytics platform, (3) a mechanism for measuring changes in variations in wind and/or current and (4) a system that analyzes the sensor data using inherent variability of air/water currents in natural settings for sensor network verification and source localization. The basics of the source attribution typically employs the following equation:

$$\begin{pmatrix} a_{0-0} & \cdots & a_{99-0} \\ \vdots & \ddots & \vdots \\ a_{0-15} & \cdots & a_{99-15} \end{pmatrix}$$

in which $$\begin{pmatrix} a_{0-0} & \cdots & a_{99-0} \\ \vdots & \ddots & \vdots \\ a_{0-15} & \cdots & a_{99-15} \end{pmatrix} \begin{pmatrix} Q_0 \\ \vdots \\ Q_{99} \end{pmatrix} = \begin{pmatrix} S_0 \\ \vdots \\ S_{15} \end{pmatrix} \underline{A} \cdot \underline{Q} = \underline{S} \quad \text{Equation (1)}$$

is the conversion matrix computed from a dispersion model.

The dispersion model may be provided by atmospheric dispersion modeling.

Atmospheric dispersion modeling is the mathematical simulation of how air pollutants disperse in the ambient atmosphere. It is performed with computer programs that solve the mathematical equations and algorithms which simulate the pollutant dispersion. The dispersion models can be used to estimate the downwind ambient concentration of air pollutants or toxins emitted from sources such as industrial plants, vehicular traffic or accidental chemical releases. In some embodiments, the dispersion models vary depending on the mathematics used to develop the model, but all require the input of data that may include 1) meteorological conditions such as wind speed and direction, the amount of atmospheric turbulence (as characterized by what is called the "stability class"), the ambient air temperature, the height to the bottom of any inversion aloft that may be present, cloud cover and solar radiation; 2) source term (the concentration or quantity of toxins in emission or accidental release source terms) and temperature of the material; 3) emissions or release parameters such as source location and height, type of source (i.e., fire, pool or vent stack) and exit velocity, exit temperature and mass flow rate or release rate; 3) terrain elevations at the source location and at the receptor location(s), such as nearby homes, schools, businesses and hospitals; and 4) the location, height and width of any obstructions (such as buildings or other structures) in the path of the emitted gaseous plume, surface roughness or the use of a more generic parameter "rural" or "city" terrain.

In some embodiments, the dispersion model may be calculated using at least one of the Gaussian air pollutant dispersion equation and/or Briggs plume rise equations. Some examples of air dispersion models used in the United States include AERMOD, CALPUFF, BLP, CALINE3, CTDMPLUS and OCD. Other examples of dispersion models include AERSCREEN, CTSCREEN, SCREEN3, TSCREEN, VALLEY, COMPLEX1, RTDM3.2, VISCREEN, Models-3/CMAQ, CAMx, REMSAD, UAM-V (Urban Airshed Model), HYSPLIT (Hybrid Single Particle-Lagrangian Integrated Trajectory Model), PUFF-PLUME, Puff model, ADMS-3, ADMS-URBAN, ADMS-Roads, ADMS-Screen, GASTAR, NAME (Numerical Atmospheric-dispersion Modelling Environment), UDM (Urban Dispersion Model), AEROPOL, Airviro Gauss, Airviro Grid. Airviro Heavy Gas, Airviro Receptor model, ATSTEP, RODOS, AUSTAL2000, BUO-FMI, CAR-FMI, CAR-International, DIPCOT, DISPERSION21, DISPLAY-2, EK100W. FARM, FLEXPART, GRAL, HAVAR, IFDM, INPUFF-U, LOTOS-EUROS, MATCH, MEMO, MERCURE, MODIM, MSS, MUSE, OML, ONM9440, OSPM, PROKAS-V, PLUME, POLGRAPH, RADM, RIMPUFF, SEVEX, STACKS, STOER.LAG, TCAM, UDM-FMI, VANADIS, AUSPLUME, pDsAUSMOD, pDsAUSMET, LADM, TAPM, DISPMOD, AUSPUFF, MLCD, Trajectory and combinations thereof.

The above dispersion models are typically used for air pollutants. As noted above, the methods used herein are equally applicable to water pollutants. For example, the dispersion model may be provided by hydrological transport model or groundwater model. In some embodiments, hydrological transport models may be provided by Hydrologic Engineering Center's River Analysis System [HEC-RAS], Arc Hydro Tools and Data Model, Arc Hydro Groundwater Toolbar, MODFLOW, PMWIN. MODFLOW Toolbox and combinations thereof. In some embodiments, the groundwater models may employ mathematical equations solved by numerical codes such as MODFLOW, ParFlow, Hydro-GeoSphere, OpenGeoSys and combinations thereof.

Still referring to equation 1, $$\begin{pmatrix} Q_0 \\ \vdots \\ Q_{99} \end{pmatrix}$$

is the possible location of sources of contaminates that can be an air pollutant or a water pollutant. Typically, an air pollutant is a substance in the air that can have adverse effects on humans and the ecosystem. The substance can be solid particles, liquid droplets, or gases. A pollutant can be of natural origin or man-made. Pollutants are classified as primary or secondary. Primary pollutants are usually produced from a process, in which examples include carbon monoxide gas from motor vehicle exhaust, or the sulfur dioxide released from factories. Secondary pollutants are not emitted directly. Rather, they form in the air when primary pollutants react or interact. Ground level ozone is a prominent example of a secondary pollutant. Some pollutants may be both primary and secondary: they are both emitted directly and formed from other primary pollutants.

One example of a primary pollutant produced by human activity is sulfur oxides ($SO_x$). In particular, sulfur dioxide, i.e., a chemical compound with the formula $SO_2$, is produced by various industrial processes. Further, coal and petroleum often contain sulfur compounds, and their combustion generates sulfur dioxide. Additionally, oxidation of $SO_2$, usually in the presence of a catalyst such as $NO_2$, forms $H_2SO_4$. Another example of a primary pollutant is nitrogen oxide, which can have the chemical formula $NO_x$. Nitrogen oxides, particularly nitrogen dioxide ($NO_2$), can expelled from high temperature combustion. Yet, another example of a primary pollutant is carbon monoxide (CO). In some examples, carbon monoxide can be the byproduct of incomplete combustion of fuel, such as natural gas, coal or wood. Vehicular exhaust is a major source of carbon monoxide. Volatile organic compounds (VOCs) are another form of primary pollutant, which can be categorized as either methane ($CH_4$) or non-methane (NMVOCs). Methane is an extremely efficient greenhouse gas that contributes to enhance global warming. Other hydrocarbon VOCs are also significant greenhouse gases, because of their role in creating ozone and prolonging the life of methane in the atmosphere. The aromatic NMVOCs benzene, toluene and xylene are also examples of air pollutants. 1,3-butadiene is another dangerous compound often associated with industrial use. Other examples of primary pollutants include particulate matter (PM), atmospheric particulate matter, or fine particles, which are tiny particles of solid or liquid suspended in a gas. In contrast, aerosol refers to combined particles and gas. Human activities, such as the burning of fossil fuels in vehicles, power plants and various industrial processes also generate significant amounts of aerosols. Other examples of primary pollutants include persistent free radicals; toxic metals, such as mercury and lead; chlorofluorocarbons; ammonia; odors, such as from garbage, sewage, and industrial processes; radioactive pollutants and any combination thereof.

Secondary pollutants may include particulates created from gaseous primary pollutants and compounds in photochemical smog. Smog is a one form of secondary air pollution. Smog can result from large amounts of coal burning in an area caused by a mixture of smoke and sulfur dioxide. Modern smog does not usually come from coal, but from vehicular and industrial emissions that are acted on in the atmosphere by ultraviolet light from the sun to form secondary pollutants that also combine with the primary emissions to form photochemical smog. Secondary pollutants may further include ground level ozone ($O_3$) that can be formed from $NO_x$ and VOCs. Ozone ($O_3$) is a key constituent of the troposphere. Peroxyacetyl nitrate (PAN) is another pollutant that is similarly formed from $NO_x$ and VOCs. Minor air pollutants that can also be detected by the systems, methods and computer products disclosed herein can include any number of minor hazardous air pollutants, such as persistent organic pollutants. Persistent organic pollutants (POPs) are organic compounds that are resistant to environmental degradation through chemical, biological, and photolytic processes.

The sources of the air pollution detected by the methods, systems and computer program products disclosed herein may be anthropogenic (man-made) sources that may be related to the burning of multiple types of fuel. The sources may be stationary sources that include smoke stacks, such as power plants, manufacturing facilities (factories) and waste incinerators, as well as furnaces and other types of fuel-burning heating devices. The sources of air pollution may be mobile sources, such as motor vehicles, marine vessels, and aircraft. In further examples, the sources of the pollutants can result from controlled burn practices in agriculture and forest management. Controlled or prescribed burning is a technique sometimes used in forest management, farming, prairie restoration or greenhouse gas abatement. Other sources of pollutants that can be measured using the methods, systems and computer products of the present disclosure include pollutants from fumes from paint, hair spray, varnish, aerosol sprays and other solvents. Addition sources for air pollution that can be measured by the methods, systems and computer program products of the present disclosure may include waste deposition in landfills; military resources; such as nuclear weapons, toxic gases, germ warfare and rocketry; and natural sources. Some examples of natural sources for air pollution generation may include dust, methane, radon gas, smoke and carbon monoxide from wildfires, VOC emitting vegetation, and volcanic activity.

In some other embodiments, the air pollutant may be natural gas and/or propane, and the pollutant source may be provided by a natural gas and/or propane leak. Natural gas is a hydrocarbon gas mixture consisting primarily of methane, but commonly includes varying amounts of other higher alkanes and sometimes a usually lesser percentage of carbon dioxide, nitrogen, and/or hydrogen sulfide. Propane is a three-carbon alkane with the molecular formula $C_3H_8$. In these examples, by determining the pollutant source, the methods, systems and structures disclosed herein may discover the source of natural gas and propane leaks.

The methods, systems and structures disclosed herein can be used to discover the source of any of the aforementioned air pollutants.

Water pollutants can be inorganic or organic, and can result from natural phenomena or man-made phenomena, such as man-made pollution. Examples of natural phenomena include volcanoes, algae blooms, storms and earthquakes. Examples of organic pollutants include detergents; disinfection by-products, e.g., chloroform: food processing waste, e.g., fats and grease; insecticides and herbicides, e.g., organohalides; petroleum hydrocarbons, e.g., fuels (gasoline, diesel fuel, jet fuels, and fuel oil) and lubricants (motor oil), and fuel combustion byproducts; volatile organic compounds, e.g., industrial solvents; chlorinated solvents, e.g., polychlorinated biphenyl (PCBs), trichloroethylene, and perchlorate, and combinations thereof. Examples of inorganic pollutants include acidity caused by industrial discharges (especially sulfur dioxide from power plants); ammonia from food processing waste; chemical waste as industrial by-products; fertilizers containing nutrients—nitrates and phosphates—which are found in storm water runoff from agriculture; heavy metals from motor vehicles (via urban storm water runoff) and acid mine drainage; silt (sediment) in runoff from construction sites, logging, slash and burn practices or land clearing sites; and combinations thereof. Water pollution may also include macroscopic pollution—large visible items polluting the water—may be termed "floatables" in an urban storm water context, or marine debris when found on the open seas, and can include such items as paper, plastic, or food waste trash garbage discarded by people on the ground, along with accidental or intentional dumping of rubbish, that are washed by rainfall into storm drains and eventually discharged into surface waters; nurdles, which are small ubiquitous waterborne plastic pellets; and combinations thereof.

The methods, systems and structures disclosed herein can be used to discover the source of any of the aforementioned water pollutants.

Referring to Equation (1), $$\begin{pmatrix} S_0 \\ \vdots \\ S_{15} \end{pmatrix}$$

is the sensor readings used for measuring pollutants. As will be described in greater detail below the sensors may be gas or chemical sensors and co-located air/water current speed and direction sensors. The sensors are to be positioned in an environment with variable air/water current speed and direction.

The methods disclosed herein typically work in the case where (1) sources, i.e., pollution sources, emit over a time scale which is long compared to the time scale at which the air/water current varies and (2) the location of a source changes slowly compared to the time scale at which air/water current varies. As will be further explained below, the methods, systems and computer program products below exploit the variability in wind, i.e., in the case of air pollution, and the variability in current, i.e., in the case of water pollution, in order to localize the source of a pollutant.

The methods, systems and structures of the present disclosure are now described with reference to FIGS. 1-6.

The method of the present disclosure typically begins with positioning a plurality of sensors throughout an area in which pollutants are to be measured. The sensors that measure pollutants may be referred to as analyte sensors. FIG. 1 is a schematic of a grid of sensors 15 across a leak area for determining a source of an air pollutant/water pollutant. The notations $S_o$, $S_{12}$, $S_3$, $S_{15}$ denote the locations of sensor readings. The notations $Q_o$, $Q_9$, $Q_{90}$, $Q_{99}$ denote the locations of possible pollutant sources. A dispersion of pollutants 14, e.g., dispersed by wind, is depicted having a source identified by reference number 13.

In the example that is depicted in FIG. 1, a 10 mile by 10 mile area is provided with a sensor 15 positioned ever 4 miles. Any air or water pollution sensor may be employed, but in the present example, the sensors were air pollution sensors 15. For example, for measuring air pollution, one common sensor is a semiconductor gas sensor. An air pollution sensor that is suitable for use with the present disclosure may include a sensing element, i.e., active element, that is exposed to the air being monitored and sensor circuitry or other components required for operation of the sensor 15. In some examples, the air pollution sensors 15 may include one or more sensors to detect gases, such as methane, ozone ($O_3$), sulfur dioxide ($SO_2$), carbon monoxide, carbon dioxide, lead (Pb), mercury (Hg), Total VOC's (TVOC's), nitric oxide (NO), nitrogen dioxide ($NO_2$), ammonia, air acidity or alkalinity, specific VOC's such as formaldehyde, or any other gases that have been described above for air pollution. As noted above, although the present example describes locating the source of air pollution, the methods disclosed herein are equally applicable to water pollution.

In some embodiments, when the air pollution sensors 15 are being employed to detect the presence of air pollutants, such as methane ($CH_4$), the sensing element of the sensor 15 may be an electrochemical cell type or a metal oxide semiconductor (MOS) type. In other embodiments, when the sensors 15 are being employed to detect the presence of air pollutants, the sensor element of the sensor 15 may be a UV adsorption active element, electrochemical cell, light scattering (mass concentration type) sensor element, light scattering (laser particle counter) sensor element or a combination thereof.

In some examples, in addition to the sensing element, i.e., active element, of the air pollution sensor 15, the sensor 15 may further include a control unit. The control unit stores the air quality (or water quality) parameter data measured by the sensors. The control unit may include a central computer and controller that control the functions of the air monitoring unit, i.e., sensing element. Those functions may include, but are not limited to, controlling the flow of air through sensor element and acquisition of sensor data, storage of sensor data in some type of nonvolatile memory or storage media, processing sensor data to provide air quality information and communicating with a remotely located control center, such as across a network. In some embodiments, the air pollution sensors 15 may incorporate a Global Positioning System (GPS) system. This allows the precise location of the sensor 15, and the pollution data monitored by the sensor 15, to be determined.

It is noted that the number of analyte sensors is selected to provide a grid, i.e., matrix, within the area that the source of a pollutant is to be localized. In the example depicted in FIG. 1, in which the area that is being measured is equal to 10 mile by 10 miles, i.e., 100 square miles, a sensor 15 is positioned using a grid layout, in which neighboring sensors are separated by 4 miles. In this example, the grid of analyte sensors is equal to 16 analyte sensors 15. It is noted that the grid of sensors 15 depicted in FIG. 1 employed in combination with the methods, systems and computer products of the present disclosure can localize the source of an air pollutant, or water pollutant, within the accuracy of 1 mile.

The above noted sensors for determining the presence of a pollutant, i.e., analyte sensors, are accompanied by sensors for measuring wind speed, i.e., air speed, and direction, and/or sensors for measuring water current, i.e., speed and direction. These sensors may be referred to collectively as current sensors. The number of current sensors that may be employed in the methods, systems and computer program products may range from being 1 current sensor within the sensing region, i.e., area within which a pollutant source is to be located, to being equal to 1 sensor per analyte sensor.

Although the example depicted in FIG. 1 includes 16 sensors 15, i.e., analyte sensors 15, any number of sensors may be employed in the system to provide a network of sensors 15 that are positioned for measuring air pollution and/or water pollution. In the example depicted in FIG. 1, a conversion matrix is computed for Equation 1, i.e., a matrix is computed from a dispersion model, e.g., computational fluid dynamics (CFD) model. For the 10 m×10 m$^2$ example described with reference to FIG. 1, a single measurement provides 16 measurements (in accordance with Equation 1) and there are 100 unknowns. Further, 7 measurements under different wind conditions provides 16 sensors×7 measurements, which equals 112 measurements, which allows for determining 100 unknowns with 1 mile accuracy. This is only one example, and it is noted that the present disclosure is not limited to only this example. Other examples, including different areas and a different number of sensors in a grid across the area are equally applicable to the present disclosure, which would provide a similar accuracy for source location determinations of pollutants.

In some embodiments, sensors 15 are in communication with a network 16. The network 16 can include a wireless network that employs the internet. For example, the network 16 may employ a local wireless connection involving a 900 MHz spread spectrum or other transmission technique commonly used in cordless phones. This technique utilizes a base unit transceiver that connects to a local phone line and another transceiver in the air pollution sensors 15. When the sensors 15 need to send or receive data, the unit checks the phone line to determine if it is busy, and if not the unit makes a call and sends or receives data through a local Internet Service Provider (ISP). Another method is to use a cellular phone to directly access a local or remote ISP. Finally, the air monitoring unit may connect to a building control system, e.g., via a WiFi connection, which is connected to the Internet to provide data to the building control system for use by this system and to connect to the Internet. It will be understood that any method of connection to the Internet may be used.

Figure 2:
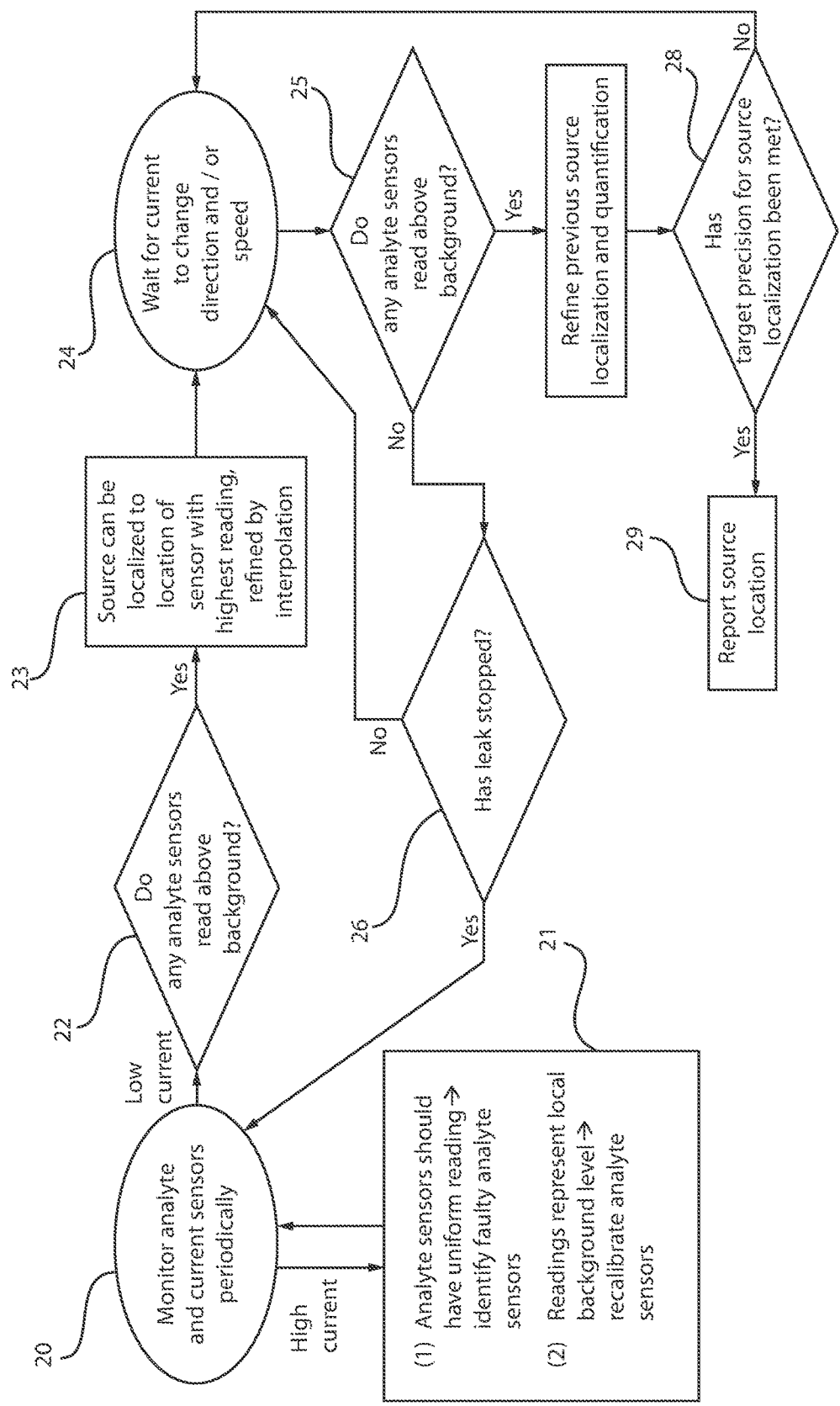
FIG. 2 is a block/flow diagram depicting one embodiment of a method of determining the source of an air pollutant/water pollutant using that a method that employs variations in wind speed and direction/variations in current speed and direction, in accordance with one embodiment of the present disclosure.
Figure 3:
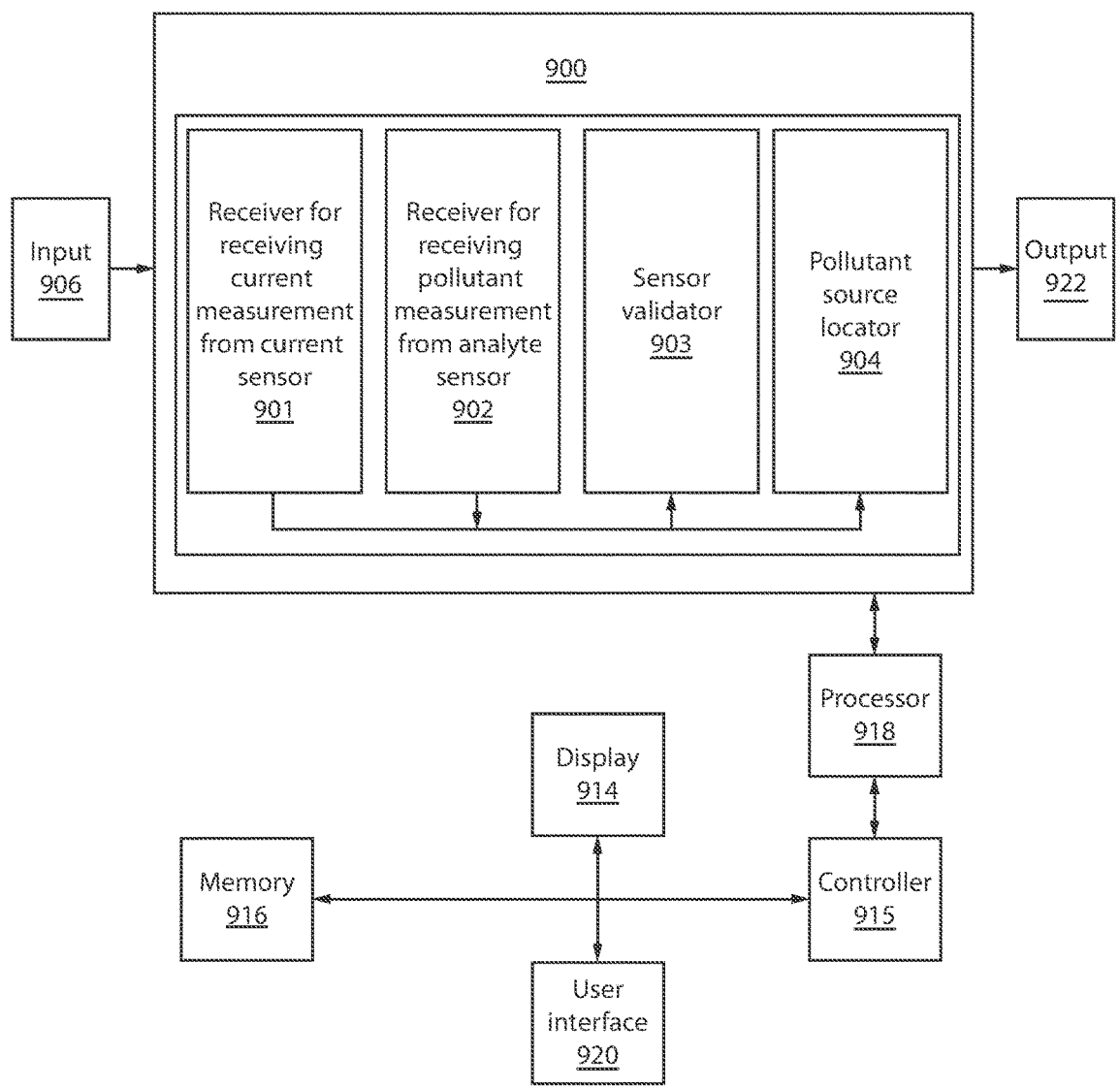
FIG. 3 is a block diagram of a system for determining the source of an air pollutant, in accordance with one embodiment of the present disclosure.

The Internet may be used to transmit information between the sensors 15 and the pollutant source localization system 900, as further described in FIG. 3, to perform pollutant localization, as described further in the process flow illustrated, in FIG. 2, based on specific information obtained about the sensors 15 in their surrounding environment positioned within the grid of the sensing area. In some embodiments, The analyte sensors 15 measure the concentration of air pollutants, tag the pollution data with relevant information, such as time, concentration and location, and send the data over a cellular data link to the pollutant source localization system 900, which can be a module on a cloud server, via the network 16, or a server at an operator of the system for determining air pollution sources.

FIG. 2 is a flow chart illustrating one embodiment of a method of determining the source of an air pollutant/water pollutants. The method employs variations in wind speed and direction/variations in current speed and direction to determine the location of pollutants. The method may employ a distributed sensor network as described with reference to FIG. 1. The sensors include analyte sensors, i.e., for detecting changes in pollutant concentration. The analyte sensors are distributed within a sending region inside which the pollutant source can be localized. The distributed sensor network further includes current, i.e., air or water, sensors. Referring to FIG. 2, the method may begin at step 20 with monitoring the analyte and current sensors, which is done periodically. In some embodiments, the reading from the current readings are analyzed for high current and low current conditions.

A high current condition measured from the current sensors at step 20 signifies that the method continues to step 21. At step 21, in response to a high current condition being measured with the current sensors, the method continues with determining if there are any faulty analyte sensors, and whether the analyte sensors need to be recalibrated. In one example, the method disclosed herein provides sensor validation by determining whether the analyte sensors have a uniform reading. In high current conditions, i.e., high air speed or high water speed, the background readings for the analyte sensors should be uniform. This is typically the case for all scenarios with the exception of very large pollutant sources, e.g., a very large leak of methane. The "background reading" for an analyte sensor is the reading at which the levels for pollutants do not exceed their normal levels in the atmosphere. For example, a pollutant composition may be normally present in the atmosphere. In this instance if the pollutant composition exceeds its normal level it is then considered at pollutant levels, i.e., above the "background reading". If the wind speed and/or water current is high enough, the analyte sensors will not be measuring any pollutants, as the pollutants are accelerated past the sensors at a speed too great for the analyte sensors to make a significant measurement. If the analyte sensors are not reading a uniform background, a problem has been detected with the sensors. In the event that the analyte sensors are not reading a correct local background level, the analyte sensors can be recalibrated.

Referring to FIG. 2, a low current condition measured from the current sensors at step 20 signifies that the method continues to step 22. At step 22, in view of the low current measured by the current sensors, the analyte sensors are monitored for measurements that the pollutant being measured by the analyte sensors exceed the background reading. If the analyte sensor reads above the background reading a pollutant is being measured. The sensor reading the pollutant provides information on the pollutant level and the location of the pollutant level on the grid in the sensor area. As depicted in FIG. 1, each sensor may be positioned on a grid in which each sensor has a specified location.

At step 23 of the method depicted in FIG. 2, from the above background reading by the analyte sensor and the position of the analyte sensor as designated on the grid within the sensing area the source of the pollutant, e.g., leak of methane, can be localized to the location of the highest reading, which can be refined by interpolation using Equation (1).

Still referring to the method depicted in the process flow illustrated in FIG. 2, the current sensors may then be monitored at step 24 for changes in current speed, e.g., air/wind speed, or water speed, and/or changes in current direction e.g., changes in air/wind direction, or changes in water flow direction.

Referring to step 25 of the process flow depicted in FIG. 2, when the current sensors measure a change in current speed, e.g., air/wind speed, or water speed, and/or changes in current direction e.g., changes in air/wind direction, or changes in water flow direction, the analyte sensors may be monitored to determine if any more of the analyte sensors are reading above the background reading.

If the same number of analyte sensors are still reading above the background reading, or none of the analyte sensors are reading above the background reading, the method may progress to step 26. At step 26, a determination is made from at least one of the analyte and current sensors of whether the pollutant source, e.g., pollutant leak, such as methane leak, that triggered the above background reading at steps 22 and 23 has stopped. If the same analyte sensors are still reading above the background reading, it is likely that the pollutant source has not stopped emitting pollutants, i.e., the pollutant leak still exists. In this scenario, the method goes back to step 24. As noted above, at step 24 the current sensors are monitored for changes in current speed, e.g., air/wind speed, or water speed, and/or changes in current direction e.g., changes in air/wind direction, or changes in water flow direction. Following step 24, the method continues through the process flow as depicted in FIG. 2, generally until the method can report a source location at step 29, as described further below.

If at step 26, none of the analyte sensors are reading above the background reading, in this scenario the pollutant source may have stopped emitting pollutants, i.e., the pollutant leak no longer exists. If the pollutant source has stopped emitting pollutants, the method may go back to step 20. In one embodiment, step 20 includes monitoring the analyte and current sensors, which may include waiting for the analyte sensors to read above background at step 22. Following steps 20 and 22, the method continues through the process flow as depicted in FIG. 1, generally until the method can report a source location at step 29, as described further below.

Referring back to step 25 of the process flow depicted in FIG. 2, if when the current sensors measure a change in current speed, e.g., air/wind speed, or water speed, and/or changes in current direction e.g., changes in air/wind direction, or changes in water flow direction, at least one of the analyte sensors may read above the background reading. In this scenario, the method may continue to step 27. At step 27, using the measurements of at least one the analyte sensors and the current sensors, in one embodiment, the method may refine the previous source localization, i.e., the source localization from step 23, using Equation (1).

At step 28, a determination is made if the target precision for source localization has been met. The target precision is a preselected value. In the example described above with reference to FIG. 1, in which the grid for the leak area is 10×10 m², and the grid of sensors includes 16 analyte sensors, seven measurements are required (between steps 23 and 27) to provide a degree of accuracy for localizing the source of pollutant down to 1 m. If the target precision for the source localization has been met, the method continues to step 29, at which the source location for the pollutant being measured/sensed is reported. If the target precision for the source localization has been met, the method goes back to step 24. As noted above, at step 24 the current sensors are monitored for changes in current speed, e.g., air/wind speed, or water speed, and/or changes in current direction e.g., changes in air/wind direction, or changes in water flow direction. Following step 24, the method continues through the process flow as depicted in FIG. 2, generally until the method can report a source location at step 29, as described further below.

In some embodiments, the methods, systems, and computer program products disclosed herein can detect the presence of gas leaks, e.g., natural gas leaks and propane gas leaks. In one example, the methods, systems and computer program products may detect the location of methane pollutant sources. It is noted that the above method is not limited to air pollutants, as water pollutants are equally applicable to the methods, systems and computer program products provided herein. In other embodiments, the methods, systems, and computer program products disclosed herein can be used to calibrate fixed sensors that are employed to measure air pollution and water pollution.

FIG. 3 depicts one embodiment of a pollutant source localization system 900 for determining the source of an air pollutant and/or water pollutant from data received from a network 16 of sensors 15, as described above with reference to FIGS. 1 and 2. In some embodiments, the pollutant source localization system 900 is typically composed of a receiver for receiving current measurements from the current sensors 901; a receiver for receiving pollutant measurements from analyte sensors 902; a sensor validator 903; and a pollutant source locator 904.

The pollutant source localization system 900 can be a tangible device that includes a hardware processor, such as the processor of a general purpose computer, or a specially designed computer having modules designed to calculate pollutant source data from the plurality of air pollutant sensors 15 that are positioned at different locations in the sensing area, as depicted in FIG. 1, relative to at least one pollution source across a network 16, or other programmable data processing apparatus. In other embodiments, the pollution source localization calculations, as typically provided by the pollutant source locator 904 of the pollutant source localization system 900, may be executed in the cloud computing environment, which can comprise at least one or more cloud computing nodes with which local computing devices, such as, for example, personal digital assistant (PDA) or cellular telephone, desktop computer, laptop computer, and/or automobile computer system may communicate. The nodes may communicate with one another. They may be grouped (not shown) physically or virtually, in one or more networks, such as private, community, public, or hybrid clouds.

In one embodiment, the pollutant source localization system 900 includes one or more processors 918 and memory 916 for storing applications, modules and other data. In one example, the one or more processors 918 and memory 916 may be components of a computer, in which the memory may be random access memory (RAM), a program memory (preferably a writable read-only memory (ROM) such as a flash ROM) or a combination thereof. The computer may also include an input/output (I/O) controller coupled by a CPU bus. The computer may optionally include a hard drive controller, which is coupled to a hard disk and CPU bus. Hard disk may be used for storing application programs, such as some embodiments of the present disclosure, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link.

The system 900 may include one or more displays 914 for viewing. The displays 914 may permit a user to interact with the system 900 and its components and functions. This may be further facilitated by a user interface 920, which may include a mouse, joystick, or any other peripheral or control to permit user interaction with the system 900 and/or its devices, and may be further facilitated by a controller 912. It should be understood that the components and functions of the system 900 may be integrated into one or more systems or workstations. The display 914, a keyboard and a pointing device (mouse) may also be connected to I/O bus of the computer. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

The pollutant source localization system 900 may receive input data 902. The input data 902 may be the pollution data measured by the plurality of air pollution sensors 15, e.g., analyte sensors that are in communication with the pollutant source localization system 900 across the network 16, as depicted in FIG. 1. Referring back to FIG. 3, the pollution data may be employed as input 906 to a plurality of modules 901, 902 of the pollutant source localization system 900, which may include a receiver for receiving current measurements from the current sensor 901 and receiver for receiving pollutant measurement from the analyte sensor 902. As noted above, the data received from the current sensor may be used at steps 20, 21 and 24 in the method for pollution source localization, as described above with reference to FIG. 2. As noted above, the data received from the analyte sensor may be used at steps 20, 21, 22, 23, 25 and 27 in the method for pollution source localization, as described above with reference to FIG. 2. Any receiver may be suitable use with the pollutant source localization system 900. Additionally, although the receiver for receiving current measurements from the current sensor 901 has been depicted as being separate from the receiver for receiving pollutant measurement from the analyte sensor 902, in some embodiments, the functions provided by these separate receivers may be integrated into a single receiver. In one embodiment, the receivers 901, 902 are configured to receive and store all the pollutant data, i.e., analyte sensor measurements and current sensor measurements, from the plurality of sensors 15, may sort and store data related to pollution composition, pollution concentration, location of sensor measuring the pollution composition and time at which the analyte sensor measured the pollution data, as well as current speed, e.g., air/wind speed, or water speed, and/or changes in current direction e.g., changes in air/wind direction, or changes in water flow direction, from the current sensors. The data sorted and stored by the receiver for receiving current measurements from the current sensor 901 and the receiver for receiving pollutant measurement from the analyte sensor 902 can be transmitted to the sensor validator 903 for sensor calibration and validation, and the pollutant source locator 904 for calculation of a pollutant source.

The sensor validator 903 may include a set (at least one) of program modules, which may be stored in memory, and may include a series of instructions (executable by a hardware processor device) for carrying out validation and calibrations of the sensors measuring pollutants, e.g., analyte sensors, in accordance with step 21 of the method described in FIG. 2. The input to the sensor validator 903 includes the data from the receiver for receiving current measurements from the current sensor 901 and receiver for receiving pollutant measurement from the analyte sensor 902.

Referring to FIG. 3, the pollution source locator 904 may localize a pollution source using the data from the receiver for receiving current measurements from the current sensor 901 and receiver for receiving pollutant measurement from the analyte sensor 902 in combination with a dispersion model. The dispersion model employed by the pollution source locator 904 may include Equation (1). The pollution source locator 904 may include a set (at least one) of program modules, which may be stored in memory and executable by at least one hardware processor, and may include a series of instructions (executable by a hardware processor device) for carrying out pollutant source localization in accordance with the method described in FIG. 2, e.g., in accordance with at least steps 23 and 27 of the method described in FIG. 2.

Referring to FIG. 3, the pollutant source localization system 900 may produce output data 922, as provided by step 29 of the method depicted in FIG. 2, which can be the source of a pollutant measured from the sensors as calculated in the pollutant source locator 904. In one embodiment, data related to the source of the pollutant calculated by the pollutant source locator 904 may be displayed on one or more display devices 914. It should be noted that while the above configuration is illustratively depicted, it is contemplated that other sorts of configurations may also be employed according to the present principles.

The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Therefore, in some embodiments, the computer readable storage medium may be referred to as being "non-transitory".

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
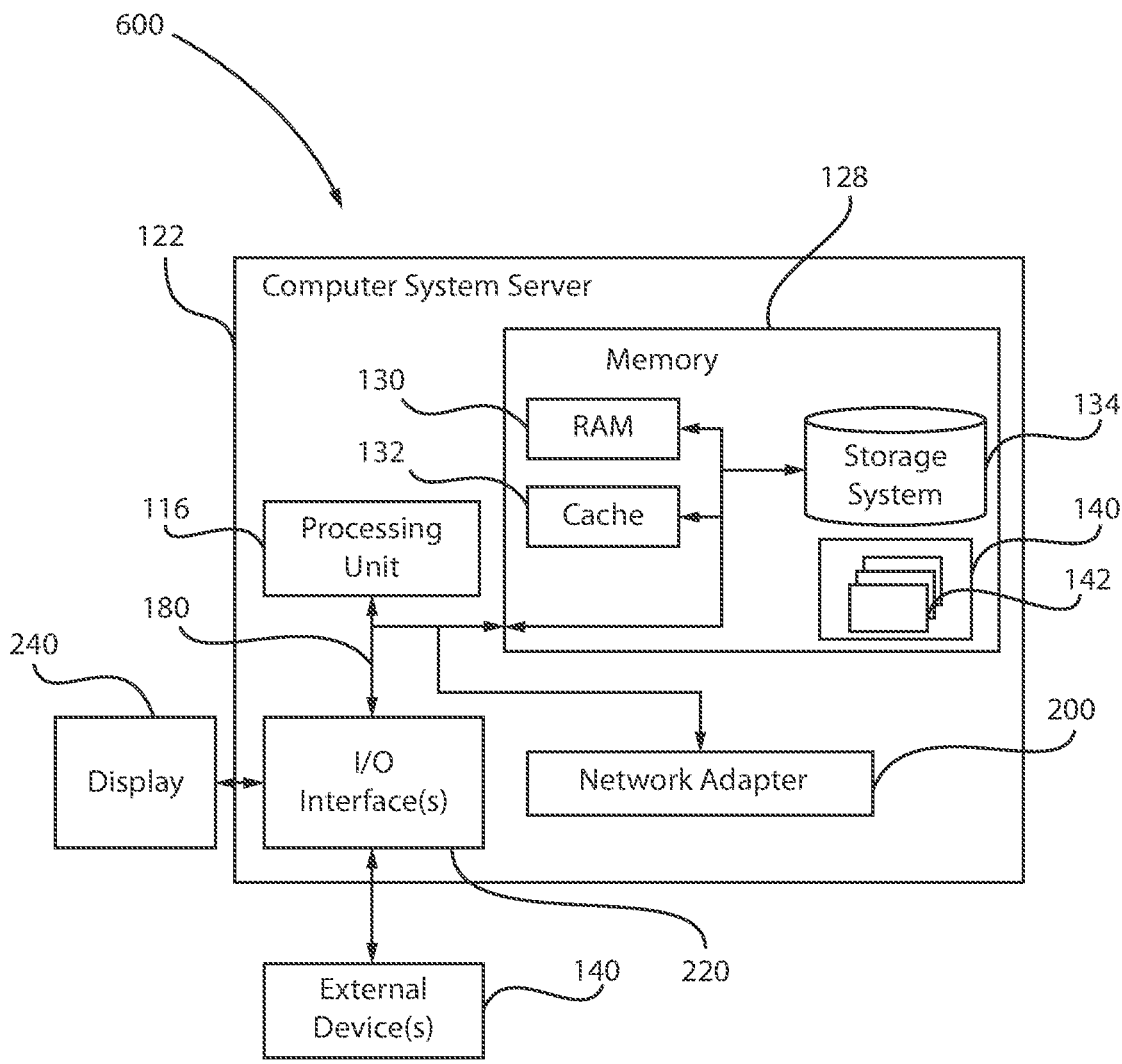
FIG. 4 depicts a cloud computing node according to an embodiment of the present disclosure.

Referring now to FIG. 4, a schematic of an example of a cloud computing node is shown. Cloud computing node 600 is only one example of a suitable cloud computing node, and is not intended to suggest any limitation as to the scope of use or functionality of embodiments of the present disclosure described herein. Regardless, cloud computing node 600 is capable of being implemented and/or performing any of the functionality set forth hereinabove.

In cloud computing node 600 there is a computer system/server 122, which is operational with numerous other general purpose or special purpose computing system environments or configurations. Examples of well-known computing systems, environments, and/or configurations that may be suitable for use with computer system/server 122 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 122 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 122 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 122 in cloud computing node 600 is shown in the form of a general-purpose computing device. The components of computer system/server 122 may include, but are not limited to, one or more processors or processing units 116, a system memory 128, and a bus 180 that couples various system components including system memory 128 to processor 116.

Bus 118 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus. Enhanced ISA (EISA) bus, Video Electronics Standards Association (VESA) local bus, and Peripheral Component Interconnects (PCI) bus.

Computer system/server 122 typically includes a variety of computer system readable media. Such media may be any available media that is accessible by computer system/server 122, and it includes both volatile and non-volatile media, removable and non-removable media.

System memory 128 can include computer system readable media in the form of volatile memory, such as random access memory (RAM) 130 and/or cache memory 132. Computer system/server 122 may further include other removable/non-removable, volatile/non-volatile computer system storage media. By way of example only, storage system 134 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM. DVD-ROM or other optical media can be provided. In such instances, each can be connected to bus 118 by one or more data media interfaces. As will be further depicted and described below, memory 128 may include at least one program product having a set (e.g., at least one) of program modules that are configured to carry out the functions of embodiments of the methods, systems and computer program products disclosure herein.

Program/utility 140, having a set (at least one) of program modules 142, may be stored in memory 128 by way of example, and not limitation, as well as an operating system, one or more application programs, other program modules, and program data. Each of the operating system, one or more application programs, other program modules, and program data or some combination thereof, may include an implementation of a networking environment. Program modules 142 generally carry out the functions and/or methodologies of embodiments of the invention as described herein. For example, the program modules 142 may carry out the functions and/or methodologies of the receiver for receiving current measurements from the current sensors 901; the receiver for receiving pollutant measurements from analyte sensors 902; the sensor validator 903; and the pollutant source locator 904, as described above with reference to FIG. 3, as well as the method, which is described above with reference to FIG. 2.

Computer system/server 122 may also communicate with one or more external devices 140 such as a keyboard, a pointing device, a display 240, etc.; one or more devices that enable a user to interact with computer system/server 122; and/or any devices (e.g., network card, modem, etc.) that enable computer system/server 122 to communicate with one or more other computing devices. Such communication can occur via Input/Output (I/O) interfaces 220. Still yet, computer system/server 122 can communicate with one or more networks such as a local area network (LAN), a general wide area network (WAN), and/or a public network (e.g., the Internet) via network adapter 200. As depicted, network adapter 200 communicates with the other components of computer system/server 122 via bus 180. It should be understood that although not shown, other hardware and/or software components could be used in conjunction with computer system/server 122. Examples, include, but are not limited to: microcode, device drivers, redundant processing units, external disk drive arrays, RAID systems, tape drives, and data archival storage systems, etc.

Figure 5:
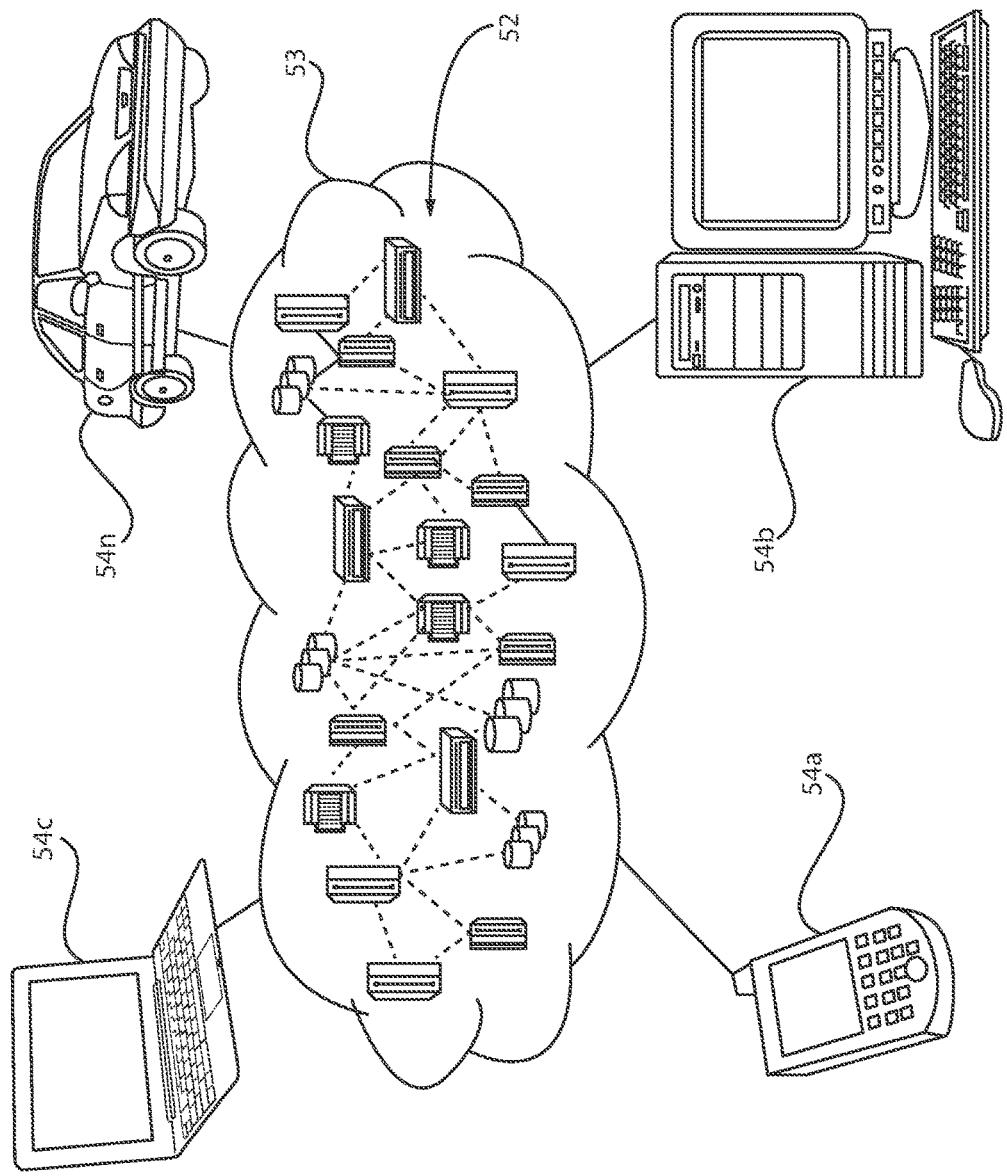
FIG. 5 depicts a cloud computing environment according to an embodiment of the present disclosure.

Referring now to FIG. 5, illustrative cloud computing environment 53 is depicted. As shown, cloud computing environment 53 comprises one or more cloud computing nodes 100 with which local computing devices used by cloud consumers, such as, for example, personal digital assistant (PDA) or cellular telephone 54A, desktop computer 54B, laptop computer 54C, and/or automobile computer system 54N may communicate. The cloud computing environment 53 may provide an interface between the pollutant source localization system 900 and the air pollution sensors employed to measure the air pollution data for localizing the source of air pollutants in accordance with the methods and systems described with reference to FIGS. 1-3.

Referring to FIG. 5, the nodes 52 may communicate with one another. They may be grouped (not shown) physically or virtually, in one or more networks, such as Private, Community, Public, or Hybrid clouds as described hereinabove, or a combination thereof. This allows cloud computing environment 52 to offer infrastructure, platforms and/or software as services for which a cloud consumer does not need to maintain resources on a local computing device. It is understood that the types of computing devices 54A-N shown in FIG. 2 are intended to be illustrative only and that computing nodes 100 and cloud computing environment 50 can communicate with any type of computerized device over any type of network and/or network addressable connection (e.g., using a web browser).

Figure 6:
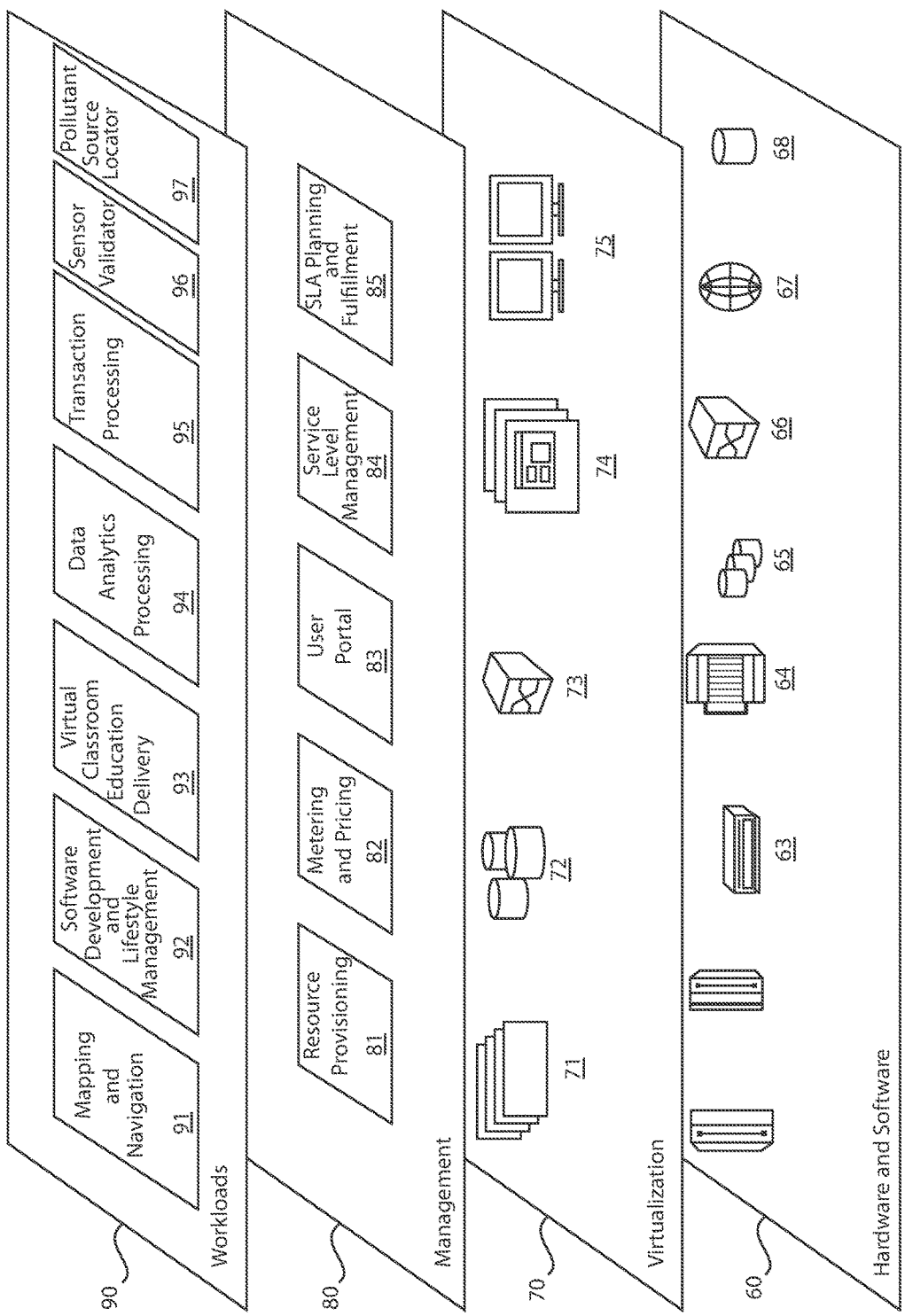
FIG. 6 depicts abstraction model layers according to an embodiment of the present disclosure.

Referring now to FIG. 6, a set of functional abstraction layers provided by cloud computing environment 53 (FIG. 5) is shown. It should be understood in advance that the components, layers, and functions shown in FIG. 3 are intended to be illustrative only and embodiments of the systems, methods and computer program are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks: virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; sensor validator 96 and pollutant source locator 97. The sensor validator 96 and the pollutant source locator 97 provided by workload layer 90 may include functions and/or methodologies of the sensor validator 903 and the pollutant source locator 904, which are described above with reference to FIG. 3.

Having described preferred embodiments of a system and method and computer program product for determining the source of air pollutants using sensors mounted to motor vehicles, it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for measuring pollution comprising:
   providing a plurality of analyte sensors arranged a sensing area;
   positioning at least one current sensor in the sensing area;
   validating operation of at least one of said analyte sensors with said at least one current sensor, wherein when said current sensor measures a current rate above a background current rate said at least one of said analyte sensors in said corresponding to said current sensor measuring said current rate above the background current can not sense accurate pollutant measurements; and
   localizing a pollution source using a pollution source locator including a dispersion model and at least one hardware processor to interpolate a location of a pollution source from variations in current measured from the current sensors and measurements of pollutants from the analyte sensors.

2. The method of claim 1, wherein said pollution comprises air pollution, water pollution or a combination thereof.

3. The method of claim 1, further comprising validating analyte sensor operation when said at least one current sensor measures a current rate.

4. The method of claim 3, wherein said validating analyte sensor operation comprises monitoring whether analyte sensors are operating at a uniform background reading.

5. The method of claim 4, wherein if said analyte sensors are operating at a uniform background reading said analyte sensors have been validated, and wherein if said analyte sensors are not operating at a uniform background reading said analyte sensors need calibration.

6. The method of claim 1, wherein said localizing the pollution source using the pollution source locator comprises:
monitoring said current sensors for changes in current speed, current direction or a combination thereof for at least two current changing events;
measuring pollutants from said plurality of said analyte sensors for each of said at least two current changing events; and
inputting data from at least one of said pollutants measured by said plurality of said analyte sensors, location of said analyte sensors reading said pollutants, and said current speed, said current direction or said combination thereof by said current sensors into said dispersion model to said interpolate said location of said pollution source.

7. The method of claim 6, wherein said dispersion model comprises:

$$\begin{pmatrix} a_{0-0} & \cdots & a_{99-0} \\ \vdots & \ddots & \vdots \\ a_{0-15} & \cdots & a_{99-15} \end{pmatrix} \begin{pmatrix} Q_0 \\ \vdots \\ Q_{99} \end{pmatrix} = \begin{pmatrix} S_0 \\ \vdots \\ S_{15} \end{pmatrix}$$

in which $$\begin{pmatrix} a_{0-0} & \cdots & a_{99-0} \\ \vdots & \ddots & \vdots \\ a_{0-15} & \cdots & a_{99-15} \end{pmatrix}$$

is a conversion matrix computed from said dispersion model, $$\begin{pmatrix} Q_0 \\ \vdots \\ Q_{99} \end{pmatrix}$$

is a possible location of sources of contaminates that can be said pollutant, and $$\begin{pmatrix} S_0 \\ \vdots \\ S_{15} \end{pmatrix}$$

are readings from the sensors.

8. The method of claim 1, wherein said pollutant is an air pollutant selected from the group consisting of sulfur oxide ($SO_x$), sulfur dioxide ($SO_2$), nitrogen oxide ($NO_x$), nitrogen dioxide ($NO_2$), sulfuric acid ($H_2SO_4$), carbon monoxide (CO), carbon dioxide ($CO_2$), volatile organic compounds (VOCs), methane ($CH_4$), non-methane volatile organic compounds (NMVOCs), particulate matter (PM), atmospheric particulate matter, fine particles, persistent free radicals, toxic metals, mercury, lead, chlorofluorocarbons, ammonia, natural gas, propane, smog (black carbon) and combinations thereof.

9. The method of claim 1, wherein said analyte sensor comprises an active element selected from the group consisting of an electrochemical cell, a metal oxide semiconductor, UV adsorption active element, light scattering sensor element, and combinations thereof.

10. A system for determining the source of a pollutant comprising:
a receiver for receiving measurements of current variations from a current sensor positioned in a sensing area, and for receiving pollutant measurements from a plurality of analyte sensors in the sensing area;
a sensor validator that determines using current measurements form the current sensor whether the analyst sensors are functioning, wherein said sensor validator validates analyte sensor operation when said current sensor measures a current rate above a background current rate so that the analyte sensor can not sense pollutant measurements; and
a pollution source locator including a dispersion model and at least one hardware processor to interpolate a location of a pollution source from variations in current measured from the current sensors and measurements of pollutants from the analyte sensors.

11. The system of claim 10, wherein said pollution comprises air pollution, water pollution or a combination thereof.

12. The system of claim 10, wherein said sensor validator validates analyte sensor operation when said current sensor measures a current rate above a background current rate, wherein said validating analyte sensor operation includes monitoring whether said analyte sensors are operating at a uniform background reading.

13. The system of claim 12, wherein if said analyte sensors are operating at a uniform background reading said analyte sensors have been validated, and wherein if said analyte sensors are not operating at a uniform background reading said analyte sensors need calibration.

14. The system of claim 12, wherein said pollution source locator monitors said current sensors for changes in current speed, current direction or a combination thereof for at least two current changing events to determine when to monitor readings from said analyte sensors when determining said location of said pollution source.

15. The system of claim 14, wherein in response to a change in at least one of the current speed and the current direction, the pollution source locator inputs data from the pollutants measured by the plurality of the analyte sensors, location of the analyte sensors reading said pollutants, and the current speed, the current direction or combination thereof by said current sensors into the dispersion model to said interpolate the location of the pollution source.

16. The system of claim 15, wherein said dispersion model comprises:

$$\begin{pmatrix} a_{0-0} & \cdots & a_{99-0} \\ \vdots & \ddots & \vdots \\ a_{0-15} & \cdots & a_{99-15} \end{pmatrix} \begin{pmatrix} Q_0 \\ \vdots \\ Q_{99} \end{pmatrix} = \begin{pmatrix} S_0 \\ \vdots \\ S_{15} \end{pmatrix}$$

in which $$\begin{pmatrix} a_{0-0} & \cdots & a_{99-0} \\ \vdots & \ddots & \vdots \\ a_{0-15} & \cdots & a_{99-15} \end{pmatrix}$$

is a conversion matrix computed from said dispersion model, $$\begin{pmatrix} Q_0 \\ \vdots \\ Q_{99} \end{pmatrix}$$

is a possible location of sources of contaminates that can be said pollutant, and $$\begin{pmatrix} S_0 \\ \vdots \\ S_{15} \end{pmatrix}$$

are readings from the sensors.

17. The system of claim 10, wherein said pollutant is an air pollutant selected from the group consisting of sulfur oxide ($SO_x$), sulfur dioxide ($SO_2$), nitrogen oxide ($NO_x$), nitrogen dioxide ($NO_2$), sulfuric acid ($H_2SO_4$), carbon monoxide (CO), carbon dioxide ($CO_2$), volatile organic compounds (VOCs), methane ($CH_4$), non-methane volatile organic compounds (NMVOCs), particulate matter (PM), atmospheric particulate matter, fine particles, persistent free radicals, toxic metals, mercury, lead, chlorofluorocarbons, ammonia, natural gas, propane, smog (black carbon) and combinations thereof.

18. The system of claim 10, wherein said analyte sensor comprises an active element selected from the group consisting of an electrochemical cell, a metal oxide semiconductor, UV adsorption active element, light scattering sensor element, and combinations thereof.

19. A non-transitory computer readable storage medium is provided that includes a computer readable program for determining a source of air pollution, the computer readable program when executed on a computer causes the computer to perform the steps of:
   receiving measurements of current variations from a current sensor positioned in a sensing area;
   receiving pollutant measurements from a plurality of analyst sensors positioned in the sensing area;
   determining at current values above a background current value that do not allow for accurate measurement of pollutants by the analyte sensors, the current values above said background current value received from the current sensors whether the analyte sensors are calibrated, wherein calibrated analyte sensors read a uniform background reading at said current values above said background current value; and
   localizing a pollution source with a pollution source locator including a dispersion model and at least one hardware processor to interpolate a location of a pollution source from variations in current measured from the current sensors and measurements of pollutants from the analyte sensors.

20. The non-transitory computer readable storage medium of claim 19, wherein said pollution comprises air pollution, water pollution or a combination thereof.

* * * * *